United States Patent
Drewe et al.

(10) Patent No.: US 11,285,187 B2
(45) Date of Patent: *Mar. 29, 2022

(54) PETASITES EXTRACT AND COMPOSITION AND METHOD FOR TREATING VIRAL INFECTIONS

(71) Applicant: MAX ZELLER SOEHNE AG, Romanshorn (CH)

(72) Inventors: Jurgen Drewe, Kreuzlingen (CH); Stephan Toff, Abtwil (CH); Catherine Zahner, Romanshorn (CH)

(73) Assignee: MAX ZELLER SOEHNE AG, Romanshorn (CH)

(*) Notice: Subject to any disclaimer, the term of this patent is extended or adjusted under 35 U.S.C. 154(b) by 107 days.

This patent is subject to a terminal disclaimer.

(21) Appl. No.: 16/697,528

(22) Filed: Nov. 27, 2019

(65) Prior Publication Data

US 2020/0093877 A1    Mar. 26, 2020

Related U.S. Application Data

(63) Continuation of application No. 15/563,367, filed as application No. PCT/EP2016/055551 on Mar. 15, 2016, now Pat. No. 10,517,912.

(30) Foreign Application Priority Data

Apr. 1, 2015   (EP) .................................... 15162229

(51) Int. Cl.
*A61K 36/28*      (2006.01)
*A61K 45/06*      (2006.01)

(52) U.S. Cl.
CPC .............. *A61K 36/28* (2013.01); *A61K 45/06* (2013.01); *A61K 2236/37* (2013.01)

(58) Field of Classification Search
CPC ....................................................... A61K 36/28
See application file for complete search history.

(56) References Cited

FOREIGN PATENT DOCUMENTS

| | | |
|---|---|---|
| CN | 103272130 | 9/2013 |
| CN | 103432457 | 10/2014 |
| DE | 19838848 | 3/2000 |
| EP | 1023079 | 8/2001 |
| EP | 1499334 | 1/2005 |
| KR | 2012-0027040 | 3/2012 |

OTHER PUBLICATIONS

Wildi et al., "Quantitative analysis of petasin and pyrrolizidine alkaloids in leaves and rhizomes of in situ grown Petasites hybridus plants," Planta Medica 64:264-267, 1998.*

Brattstrom, et al., "A newly developed extract (Ze 339) from butterbur (*Petasites hybridus* L.) is clinically efficient in allergic rhinitis (hay fever)", Phytomedicine, Gustav Fischer Verlag, Stuttgart, De., vol. 10, Jan. 1, 2003, pp. 50-52, XP004957128.

(Continued)

*Primary Examiner* — Rosanne Kosson
(74) *Attorney, Agent, or Firm* — Bryan D. Zerhusen, Esq.; Nicholas R. Herrel, Esq.; Cantor Colburn LLP

(57) ABSTRACT

The present invention relates to a *Petasites* extract or pharmaceutical composition thereof for use in a method for treating viral infections.

17 Claims, 5 Drawing Sheets

(56) References Cited

OTHER PUBLICATIONS

Brattstrom, et al.,, "Petasites Extract Ze 339 (PET) Inhibits Allergen-induced TH2 Responses, Airway Inflammation and Airway Hyperractivity in Mice", 2010, Phytother. Res., 24, 680-5.

Christen and Fritz Vogtle, Organische Chemie—Von den Grundlagen sur Forschung—vol. 1., 36-37, 1988 (With Translation).

Dumitru, et al., "Petasol Butenoate Complex (Ze 339) relieves allergic rhinitis-induced nasal obstruction more effectively than desloratadine", 2011, J. Allergy Clin. Immunol., 127, 1515-21.

Fortier, et al., "The Viral Mimic, Polyinosinic: Plycytidylic acid, induces fever in rats via an interleukin-1-dependent mechanism", 2004, Am. J. Physiol. Regul. Intergr. Comp. Physiol., 287, R759-66.

Gitlin, L., et al., "Essential role of mda-5 in type I IFN responses to polyriboinosinic: Polyribocytidylic acid and encephalomyocarditis picornavirus", 2008, PNAS, 103, 8459-8464.

Kato H., et al., "Cell Type-specific involvement of RIG-I in antiviral response", 2005, Immunity, 23, 19-28.

Kato, H., et al., "Length-dependent recognition of double-stranded ribonucleic acids by retinoic acid-inducible gene-I and melanoma differentiation-associated gene 5", 2008, J. Exp. Med. 205, 1601-1610.

Kaufeler, et al., "Efficacy and Satety of Butterbur Herbal Extract Ze 339 in seasonal allergic rhinitis: Postmarketing surveillance study", 2006, Adv. Ther., 23, 373-84.

Keusch, et al., "Treatment of allergic Rhinitis with the special butterbur extract Ze 339", 2004, Ars Medici, pp. 509-515.

Lee, J, et al., "Activation of Innate Immunity is Required for Efficient Nuclear Reprogramming", 2012, Cell, 151, 547-558.

Nebel, et al., "Effective treatment of early allergic and late inflammatory symptoms of allergic rhinitis with Ze 339 (Tesalin® n): Results of a non-interventional observational study", 2014, Planta Med., 80—P1C24.

Schapowal, et al., "Butterbur Ze 339 for the treatment of intermittent allergic rhinitis", 2004, Arch. Otolaryngol. Head Neck Sur., 130, 1381-6.

Schapowal, et al., "Randomised controlled trial of butterbur and cetirizine for treating seasonal allergic rhinitis", Jan. 19, 2002, BMJ, 324, 1-4.

Schapowal, et al.,"Treating intermittent allergic rhinitis: a prospective, randomized, placebo and antihistamine-controlled study of butterbur extract Ze 339", 2005, Phytother. Res., 19 530-7.

Thomet, et al., "Anit-inflammatory activity of an extract of Petasites hybridus in allergic rhinitis", 2 (2002), Intern. Immunopharacol, pp. 997-1006.

Vogl, et al., "Ethnophamacological in vitro studies on Austria's folk medicine—An unexplored lore in vitro anti-inflammatory activities of 71 Austrian traditional herbal drugs", Journal of Ethnophamacology, 149: 750-771, 2013.

U.S. Appl. No. 15/563,367, filed Sep. 29, 2017, US 2018-0078594 A1.

* cited by examiner

PETASITES EXTRACT AND COMPOSITION AND METHOD FOR TREATING VIRAL INFECTIONS

CROSS-REFERENCE TO RELATED APPLICATIONS

This application is a continuation application of U.S. patent application Ser. No. 15/563,367, filed on Sep. 29, 2017, which is a U.S. national entry of International Application PCT/EP2016/055551, titled: "*PETASITES* EXTRACT AND COMPOSITION AND METHOD FOR TREATING VIRAL INFECTIONS", having an International filing date of Mar. 15, 2016; which claims the benefit of European Patent Application Serial No. EP 15162229.7, filed Apr. 1, 2015; the entire contents of the aforementioned applications are hereby incorporated herein by reference.

BACKGROUND OF THE INVENTION

Viral infections constitute a widely spread disease caused by a large number of different viruses. In animals, in particular mammals, viral infections typically lead to inflammation reactions in their hosts as part of the immune defence response. Said inflammation reactions can cause discomfort and, in certain cases, further medical complications in the infected subject. Hence, it is desirable to reduce the inflammation brought about by viral infections.

The plant *Petasites* is commonly also referred to as Butterbur and *Petasites* extracts can be gained from the plant, in particular from the leaves and/or the rhizome. The production of *Petasites* extracts is well known in the art. However, depending on the extraction protocol the extracts can comprise pyrrolizdine-alkaloids which can be hepatotoxic, carcinogenic and mutagenic.

*Petasites* extracts are known to display spasmolytic and analgesic properties. DE-A1 198 38 848 discloses *Petasites* extracts for use in the treatment of gastrointestinal diseases, asthma, pollinosis, dysmenorrhoea, eczemas, migraine, psoriasis, high blood pressure and/or spasms. EP 1 499 334 B1 describes the use of a polar *Petasites* extract for use in the treatment of pains. The use of *Petasites* extracts for treating allergic rhinitis is described in the art. For further information on the medical utility of *Petasites* extracts reference is made to, e.g. Schapowal et al., 2002, BMJ, 324, 144-6; Thomet et al., 2002, Intern. Immunopharmacol.; Brattström et al., 2003, Phytomedicine, 10, Suppl 4, 50-2; Schapowal et al., 2004, Arch. Otolaryngol. Head Neck Surg., 130, 1381-6; Schapowal et al., 2005, Phytother. Res., 19, 530-7; Keusch et al., 2004, Ars Medici; Käufeler et al., 2006, Adv. Ther., 23, 373-84; Brattström et al., 2010, Phytother. Res., 24, 680-5; Dumitru et al., 2011, J. Allergy Clin. Immunol., 127, 1515-21; and Nebel et al., 2014, Planta Med., 80).

The objective underlying the present invention is the provision of a new composition for treating viral infections, preferably viral respiratory tract or viral skin infections.

It was surprisingly found that an extract from *Petasites* has excellent utility for use in the treatment of viral infections.

Therefore, in a first aspect, the invention is directed to a *Petasites* extract for use in the treatment of a viral disease.

Generally, the term "extract" as used in the art and herein refers to any product of extraction regardless of the final chemical composition or physical form, e.g. liquid, viscous, pasty or solid. Of course, a plant extract for pharmaceutical use is understood to relate to a plant extract product comprising the active plant agent(s) in a physiologically effective form and amount. Typically, a solvent-based extraction, e.g. aqueous, non-aqueous, liquid, gaseous, critical gas, e.g. sub- or supercritical carbon dioxide extraction, will result in extracted components that are optionally separated from the remaining raw materials, e.g. separated from the remaining solid plant materials, and which components can optionally be further processed, e.g. purified. A preferred and non-limiting exemplary protocol for the manufacture of a *Petasites* extract for use in the present invention is described in Example 1.

Depending on the type and mode of extraction, a *Petasites* extract can also comprise toxic pyrrolizidine-alkaloids and pyrrolizidine-alkaloid derivatives such as N-oxides to a varying extent. In a preferred embodiment, the *Petasites* extract for use in the present invention is substantially free of pyrrolizidine-alkaloids including any derivatives of pyrrolizidine-alkaloids such as, e.g. N-oxides. Substantially free of pyrrolizidine-alkaloids means that the *Petasites* extract comprises non-toxic amounts of pyrrolizidine-alkaloids, preferably <2 ppm pyrrolizidine-alkaloids, more preferably <1 ppm pyrrolizidine-alkaloids, most preferably no pyrrolizidine-alkaloids.

Generally, *Petasites* extracts can be distinguished into polar and non-polar *Petasites* extracts. In a preferred embodiment, the extract for use in the invention is a non-polar *Petasites* extract, preferably one produced by extraction with liquid carbon dioxide, more preferably by extraction with liquid carbon dioxide at subcritical temperature conditions. Subcritical temperature conditions in the context of carbon dioxide extraction are preferably extraction temperatures <31° C., more preferably extraction temperatures between 0 to 30° C. For example, an extraction of *Petasites* using a subcritical carbon dioxide extraction protocol to obtain non-polar *Petasites* extracts for use in the present invention is described in European patent EP 1 023 079 B1.

In an alternative preferred embodiment, the extract for use in the invention is a polar *Petasites* extract, preferably a polar *Petasites* extract which is substantially free of pyrrolizidine-alkaloids, more preferably a polar *Petasites* extract having an Rf value (TLC, silica gel 60, eluent toluene/ethyl acetate 93:7) of 0 to 0.21, e.g. as described in granted European patent EP 1 499 334 B1. An example of a procedure for the TLC analysis of *Petasites* extracts is described in detail in Example 2 below. The principle method of TLC analysis is well known to the skilled person and is, for example, described in Hans Rudolf Christen and Fritz Vögtle, "Organische Chemie—von den Grundlagen zur Forschung—Volume 1, 36-37, 1988.

The capacity of an exemplary *Petasites* extract to reduce virus-mediated inflammations is demonstrated in Examples 3 and 4 below, where polyinosinic:polycytidylic acid (Poly IC) and also Poly IC LyoVec™ (InvivoGen, France) are used in human nasal epithelial cells ex vivo as immunostimulants to simulate viral infections (Fortier et al., 2004, Am. J. Physiol. Regul. Integr. Comp. Physiol., 287, 759-66). This model is generally accepted in the art as being representative for a viral infection in mammals, in particular humans. As read-out for inflammation, the expression levels of the cytokines granulocyte-colony stimulating factor (GCSF), macrophage inflammatory proteins (MIP-1α and MIP-1β), interleukin 6 (IL-6), interleukin 1α (IL-1α), tumor necrosis factor α (TNF-α) and chemokine (C—C-motif) ligand 5 (CCL5) were used with and without the co-administration of the polar *Petasites* extract "Tesalin" (Max Zeller Soehne A G, Romanshorn, Schweiz).

Surprisingly, the effectiveness of the non-polar *Petasites* extract "Ze 339" ("Tesalin", Max Zeller Söhne A G) was specific to virus-mediated inflammations. When the above experiments were performed using the bacterial inflammatory stimulants bacterial lipoprotein analog Pam(3)CSK(4), Flagellin or bacterial CpG-oligonucleotide, no decrease in cytokine expression was observed upon co-administration of the polar *Petasites* extract "Ze 339" (see Example 5).

The *Petasites* extract for use in the present invention is not limited to any specific *Petasites* species because substantially all of the *Petasites* plants comprise qualitatively the same physiologically active ingredients. Therefore, and in a further preferred embodiment, the invention is directed to the use of *Petasites* extracts obtained from plants and/or parts of plants selected from the group consisting of *Petasites hybridus, Petasites albus, Petasites amplus, Petasites fragrans Petasites formosanus, Petasites frigidus, Petasites georgicus, Petasites japonicus, Petasites laevigatus, Petasites kalbikianus, Petasites niveus, Petasites paradoxus, Petasites pyrenaicus, Petasites tricholobus, Petasites radiates, Petasites sagittatus* and *Petasites spurius*.

It is further preferred that the *Petasites* extracts for use in the present invention are used in the treatment of a viral respiratory or viral skin disease.

The viral respiratory disease to be treated is preferably selected from the group consisting of exacerbation of virus-caused chronic inflammatory airway diseases, virus-caused chronic sinusitis, virus-caused sine nasal polyps, rhinovirus infections, influenza and parainfluenza infections, respiratory syncytical virus (RSV) infections, adenovirus infections, herpes virus family infections, preferably herpes simplex and herpes zoster, rotavirus infections, enterovirus, preferably coxsackie virus, human papilloma virus (HPV) infections. More preferably the viral respiratory disease to be treated is selected from the group consisting of virus-caused upper aerodigestive and sinunasal tract diseases including otitis media with and without effusion, rhinitis, rhinosinusitis, gingivostomatitis, aphtosis, pharyngitis, tonsillitis, tonsillopharyngitis, laryngitis, tracheitis, bronchitis, bronchopneumonia, pneumonia, influenza, coryza and common-cold.

The viral skin disease to be treated according to the invention is preferably selected from the group consisting of herpes family type 1 and 2 infections, herpes zoster lesions, preferably herpes infections in the context of atopic excema, molluscum contagiosum, and human papilloma virus (HPV)-associated lesions, more preferably HPV-caused condylomata and verrucae including high- and low risk serotypes.

The present invention is suitable for treating all virus-induced inflammatory responses and has so far been experimentally validated for the receptor-related inflammatory pathways associated with the toll-like receptor (TLR) family and retinoic acid inducible gene I (RIG-I)-like receptor family. In another preferred embodiment, the viral disease to be treated according to the invention is preferably a viral disease that results in an inflammation involving a receptor selected from the group consisting of the toll-like receptor (TLR) family and the retinoic acid inducible gene I (RIG-I)-like receptor family, more preferably toll-like receptor 3 (TLR3), RIG-I and melanoma differentiation-associated protein 5 (MDA5). More preferably, the viral disease is an RNA virus disease.

The extract for use in the present invention can constitute or be formulated into a pharmaceutical composition. Therefore, in another aspect, the present invention is also directed to a pharmaceutical composition for treating viral infections comprising a *Petasites* extract, and optionally a physiologically acceptable excipient.

An extract or a pharmaceutical composition, i.e. a medicament for use according to the invention typically comprises an extract of *Petasites* in a pharmaceutically effective amount suitable for administration, optionally formulated together with conventional pharmaceutically acceptable additives, carriers, adjuvants and excipients and/or further pharmaceutically active agents. Such carriers, adjuvants and excipients include, for example, ion exchangers, alumina, aluminium stearate, lecithin, serum proteins, buffer substances, water, salts, electrolytes and cellulose-based substances. Also, maltodextrin or silica can be used to produce a free-flowing dry extract which is particularly suitable for further processing. Controlled release dosage forms with or without immediate release portions are also envisaged. Methods for preparing such dosage forms are known (see, for example, H. C. Ansel and N. G. Popovish, Pharmaceutical Dosage Forms and Drug Delivery Systems, 5th ed., Lea and Febiger (1990)). Dosage levels and requirements are well-recognized in the art and may be selected by those of ordinary skill in the art from available methods and techniques suitable for a particular patient. One skilled in the field of preparing formulations can readily select the proper form and mode of administration for a *Petasites* extract for use in the present invention depending upon the particular characteristics of the extract product selected, the virus disease or virus-related condition to be treated, the stage of the disease or condition, the specific patient and other relevant circumstances (see. e.g. Remington's Pharmaceutical Sciences, Mack Publishing Co. (1990)).

As the person skilled in the art will appreciate, lower or higher doses may be required depending on particular factors. For instance, specific doses and treatment regimens will depend on factors such as the patient's general health profile, the severity and course of the patient's disorder or disposition thereto, and the judgment of the treating physician which includes interaction potentials with other needed medication.

In a preferred embodiment the pharmaceutical composition for use in the present invention comprises 5 to 600 mg *Petasites* extract, preferably 10 to 500 mg, more preferably 200 to 300 mg, depending of course on the intensity of treatment required.

Although one dose per day may be sufficient, up to 5 or more doses per day may be applied. e.g. orally or intranasally. More preferably, up to 3 doses per day may be administered. As the person skilled in the art will appreciate, lower or higher doses may be required depending on particular factors.

Next to pharmaceutically acceptable agents, the extract or composition for use according to the invention can also comprise additional physiologically active agents. Hence and in a further preferred embodiment, the pharmaceutical composition for use in the invention may additionally comprises at least one ingredient selected from the group consisting of antiphlogistic, analgesic, fever reducing agents;

extracts of *Chamomilla recutita*, rhizome *curcumae longae*, rhizome *curcumae* conthorrhizae, *curcumae* conthorrhiza, *cortex salicis, salicis purpurea, salicis daphenoides, Tanacetum parthenium;* trace elements, preferably salts of iron, iodine, copper, cobalt, magnesium, manganese, selenium, zinc;

secretolytic, secretomotoric agents, preferably extracts of the licorice root, thyme, peppermint oil;

bronchospasmolytic agents, preferably extracts of ivy leaves, calendula, viola;

vitamins, preferably vitamin A, B, C, D, E, K;

antioxidants, preferably lutein, zeaxanthin, bioflavonoids, grape seed extract; and taste mediators, preferably an artificial or natural agent, more preferably a sweetening agent, most preferably a sugar or polyol sweetener.

The extracts for use in the present invention can be administered the same way as other chemical drugs or plant extracts and pharmaceutical compositions thereof.

In a preferred embodiment, the extract or pharmaceutical composition for use according to the invention is administered orally, topically, subcutaneously, intraperitoneally, intravenously, intranasally, by inhalation or as a spray, preferably orally, by inhalation, topically or intranasally.

It is preferred that the extract or pharmaceutical composition for use according to the invention is a dosage form selected from the group consisting of a spray, an aerosol, a foam, an inhalant, a powder, a tablet, a capsule, a soft gelatin capsule, a tea, a syrup, a granule, a chewable tablet, a salve, a cream, a gel, a suppository, a lozenge, a liposome composition or a solution suitable for injection, preferably a time-release or sustained-release dosage form of the above.

While all types of application of the medicament are believed to be suitable for use according to the invention, oral, topical, inhalatory and intranasal administrations are preferred for many purposes, and the extract can be used as such or in dilution with solid and/or liquid additives and/or contain additives, carriers, adjuvants, excipients and/or other pharmacologically active constituents.

In a more preferred embodiment, the extract or pharmaceutical composition for use according to the invention is a dosage form selected from the group consisting of a tablet, a capsule, a powder, a granule, a tea, a syrup, an aerosol, an inhalant, a spray, and a time-release or sustained-release dosage form of the above.

In another aspect, the invention is directed to a method for the treatment of a viral infection, preferably a viral respiratory tract infection or a viral skin infection, more preferably a viral rhinitis or viral sinusitis, comprising the step of administering a *Petasites* extract or composition thereof, preferably a *Petasites* extract or composition for a use as described above, to a mammal, preferably a human in need thereof in an effective amount.

The term "treatment" as used herein relates to the prophylactic and/or therapeutic treatment of a disease or medical condition. For example, the extract or composition for use according to the present invention can be administered before or after a viral infection in order to inhibit and/or alleviate virus-induced physiological consequences, in particular virus-induced inflammatory reactions.

In the following the invention will be illustrated in more detail by practical examples and with reference to figures, none of which are to be interpreted as limiting the scope of the invention beyond the claims as appended.

EXAMPLES

Example 1—Preparation of Non-Polar *Petasites* Extract "Ze 339"

Accurately weighed amounts of milled *Petasites* hybridus leaves and adsorbent were transferred into extraction vessels of the carbon dioxide extraction plant. Subcritical carbon dioxide extraction was performed under pressure at a pre-defined temperature for 2-3 h with a defined amount of carbon dioxide per kg herbal substance and a defined carbon dioxide flow. In the following process step extract and carbon dioxide were separated under pressure at a defined temperature. During separation sub-batches of the native extract were collected in a stainless steel container. After separation, the extracts were homogenized by mixing at a maximum temperature of 40° C. Homogenisation was performed until the solution was clear and all carbon dioxide was evaporated.

Example 2—TLC Analysis of *Petasites* Extracts

Methods: 5 μl of a *Petasites* extract sample (5 μl of a polar *Petasites* extract (*P. hybridus* ethanolic extraction, lower phase), 5 μl of a polar *Petasites* extract (*P. hybridus* ethanolic extraction, solvent-extracted with rape oil), 5 μl of an non-polar *Petasites* extract (*P. hybridus* ethanolic extraction, upper phase), 5 μl of a non-polar *Petasites* extract (*P. hybridus* leaves native extract from carbon dioxide extraction)), which contained 5 mg *Petasites* extract sample per 1 mL methanol were added on the start line of a thin-layer chromatography (TLC) silica gel 60 F254 glass plate (obtained from the company Merck). Isopetasin and linoleic acid were co-spotted on the plates as reference compounds. After the samples had air-dried on the TLC plate, the plate was positioned in a TLC glass chamber prefilled with the eluent (toluene/ethyl acetate in a ratio of 93:7) and eluted without chamber saturation at room temperature. The TLC chamber was closed with a lid. After the solvent front had travelled a distance of 5.6 cm on the TLC plate, determined from the start line, the TLC plate was removed from the chamber and dried at 140° C. on a heating plate for approximately 30 seconds, the TLC plate was immersed in a dipping reagent (Anisaldehyde:acetic acid:methanol:sulphuric acid=0.5:10:85:5 (V/V/V/V)) and develop at 140° C. on a heating plate for approximately 50 seconds. The chromatographically separated substances were detected by irradiation of day light as well as of light at 254 nm and 366 nm wave length.

Figure 1A:
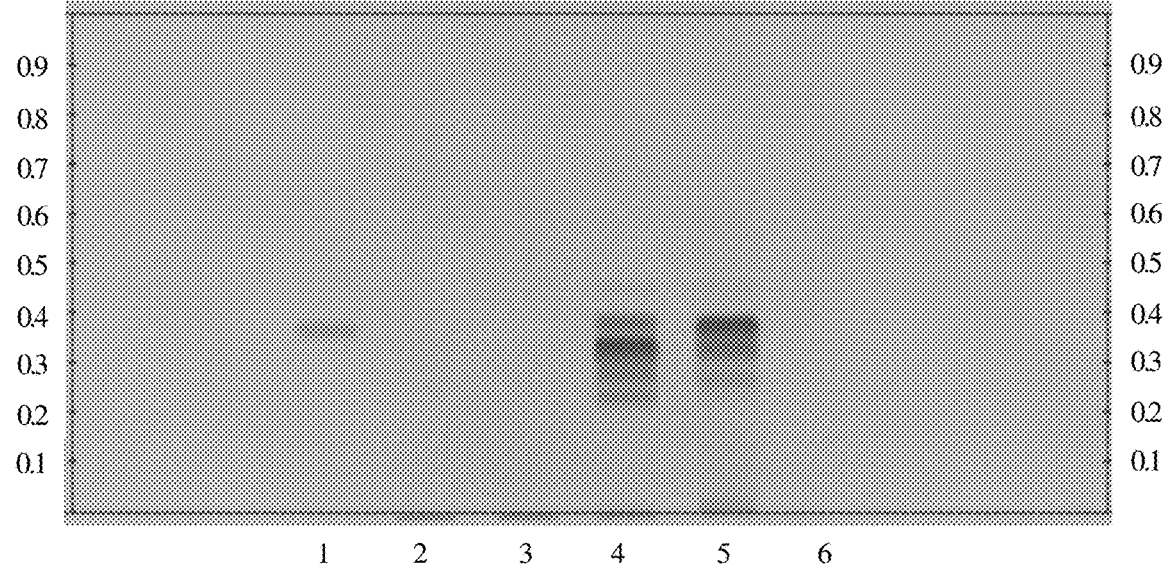
FIGS. 1a to c show TLC plates (silica gel 60, eluent toluene/ethyl acetate 93:7) of different *Petasites* extracts visualized at 254 nm wavelength (1a), under day light (1b) and at 366 nm wavelength (1c). Legend: Lane 1: reference: isopetasin, Lane 2: polar *Petasites* extract (*P. hybridus* ethanolic extraction, polar phase), Lane 3: polar *Petasites* extract (*P. hybridus* ethanolic extraction, solvent-extracted with rape oil), Lane 4: non-polar *Petasites* extract (*P. hybridus* ethanolic extraction, non-polar phase), Lane 5: non-polar *Petasites* extract (*P. hybridus* leaves native extract from carbon dioxide extraction), Lane 6: reference: linoleic acid
Figure 1B:
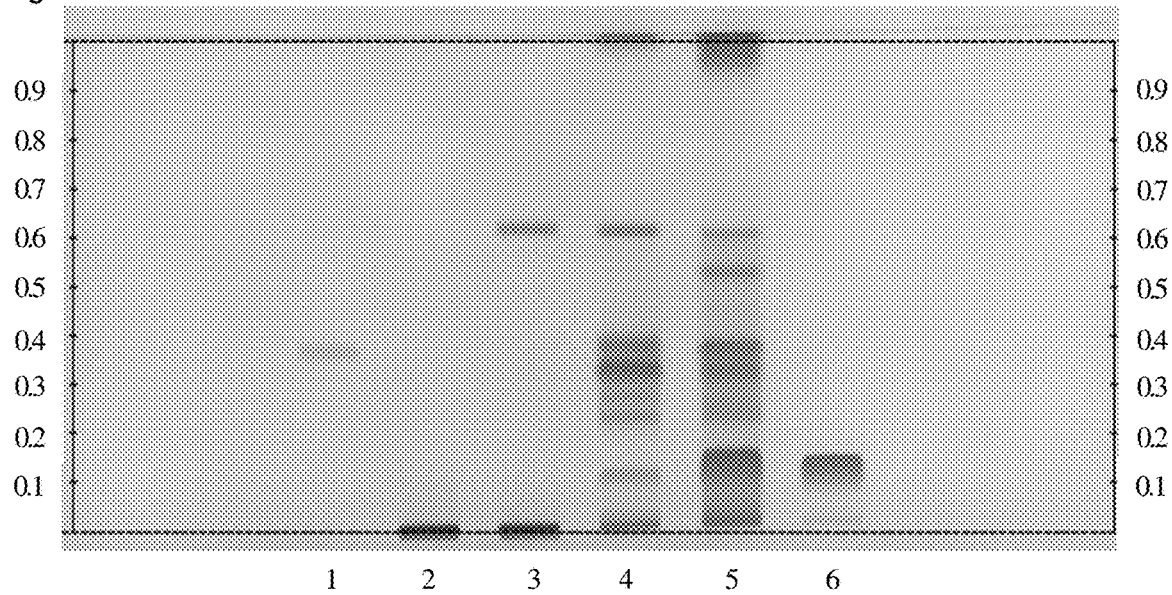
Figure 1C:
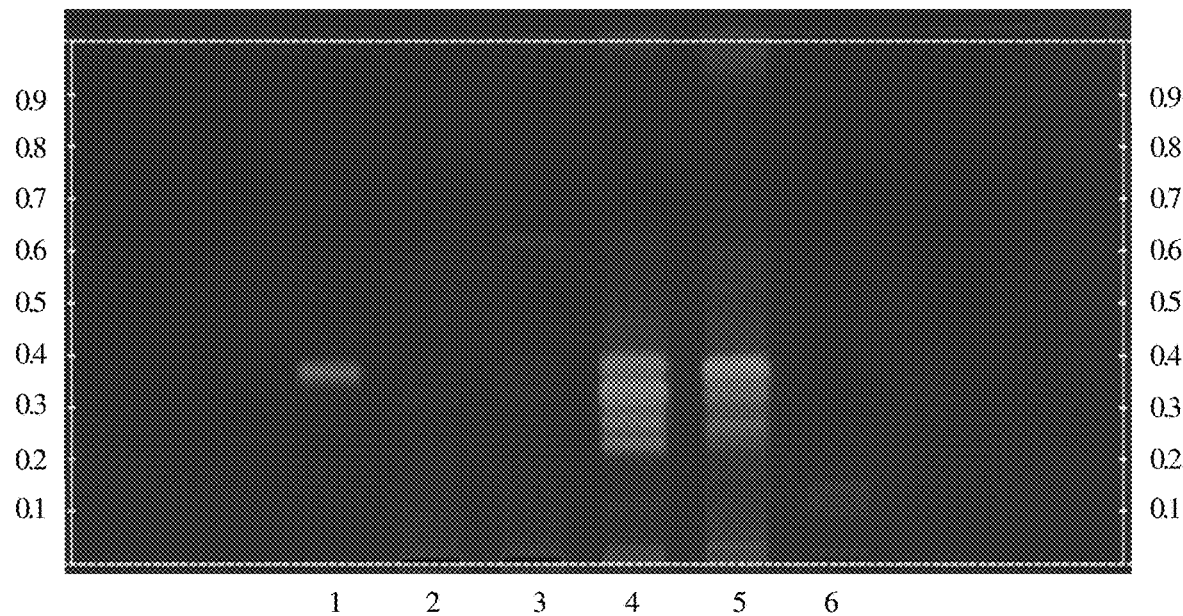
Figure 2:
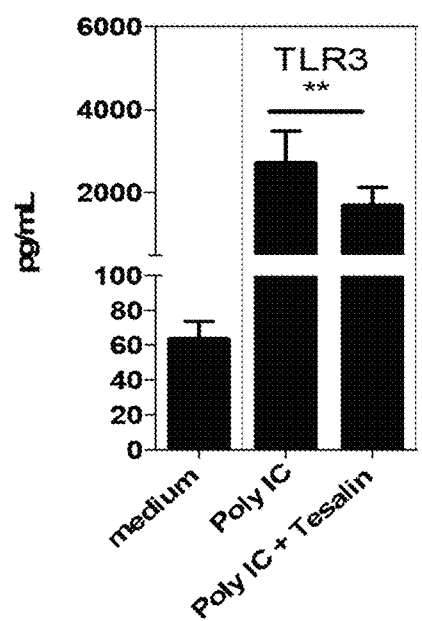
FIG. 2 shows the expression level of granulocyte-colony stimulating factor (GCSF) in nasal epithelial cells 24 h after administration of either polyinosinic:polycytidylic acid (Poly IC) with or without co-administration of the non-polar *Petasites* extract "Ze 339" ("Tesalin"). The asterisks indicate a p-value of 0.01 at n=5-8.
Figure 3:
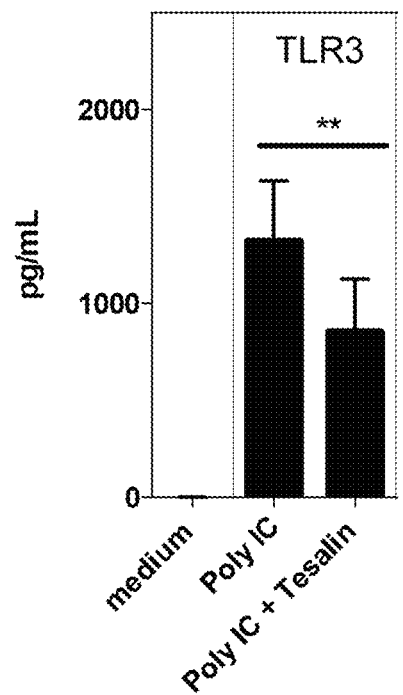
FIG. 3 shows the expression level of macrophage inflammatory protein 1β (MIP-1 β) in nasal epithelial cells 24 h after administration of either polyinosinic:polycytidylic acid (Poly IC) with or without co-administration of the non-polar *Petasites* extract "Ze 339" ("Tesalin"). The asterisks indicate a p-value of 0.01 at n=5-8.
Figure 4:
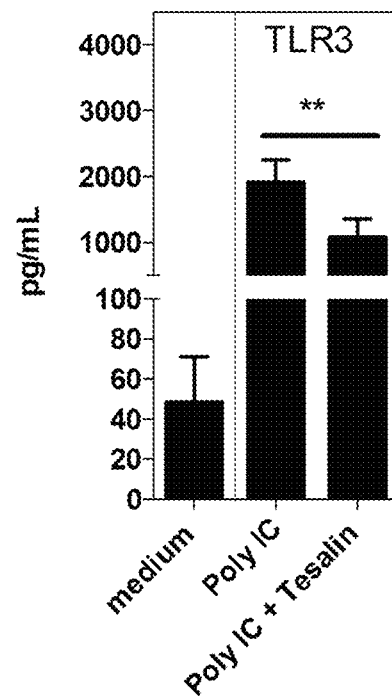
FIG. 4 shows the expression level of interleukin 6 (IL-6) in nasal epithelial cells 24 h after administration of either polyinosinic:polycytidylic acid (Poly IC) with or without co-administration of the non-polar *Petasites* extract "Ze 339" ("Tesalin"). The asterisks indicate a p-value of 0.01 at n=5-8.
Figure 5:
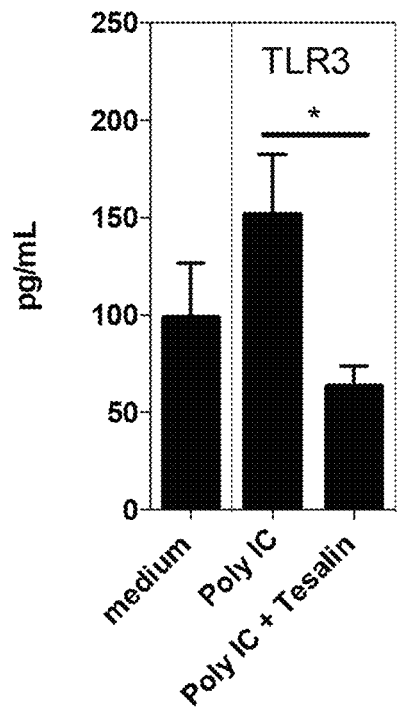
FIG. 5 shows the expression level of interleukin 1α (IL-1α) in nasal epithelial cells 24 h after administration of either polyinosinic:polycytidylic acid (Poly IC) with or without co-administration of the non-polar *Petasites* extract "Ze 339" ("Tesalin"). The asterisks indicate a p-value of 0.05 at n=5-8.
Figure 6:
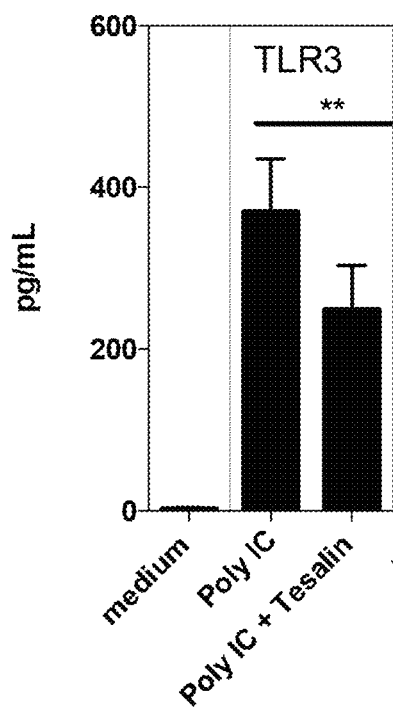
FIG. 6 shows the expression level of tumor necrosis factor α (TNF-α) in nasal epithelial cells 24 h after administration of either polyinosinic:polycytidylic acid (Poly IC) with or without co-administration of the non-polar *Petasites* extract "Ze 339" ("Tesalin"). The asterisks indicate a p-value of 0.01 at n=5-8.
Figure 7:
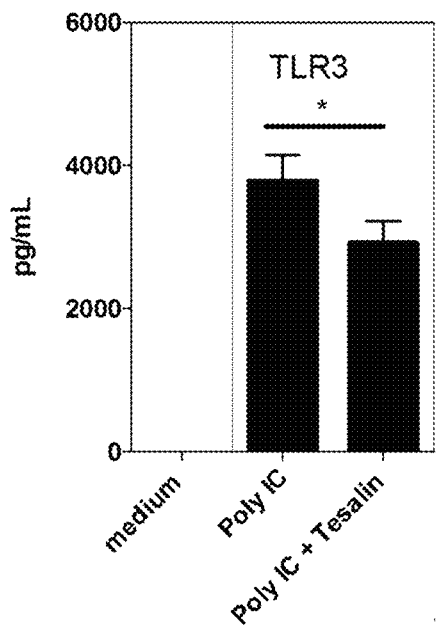
FIG. 7 shows the expression level of chemokine (C—C-motif) ligand 5 (CCL5) in nasal epithelial cells 24 h after administration of either polyinosinic:polycytidylic acid (Poly IC) with or without co-administration of the non-polar *Petasites* extract "Ze 339" ("Tesalin"). The asterisks indicate a p-value of 0.05 at n=8.

Results: FIGS. 1a to c show images of the TLC plates. Polar *Petasites* extracts (Lanes 2 and 3) only comprise components with Rf values of about 0. Non-polar *Petasites* extracts additionally show a multitude of components with Rf values between 0.1 and 1. Also, isopetasine (as an example for a petasine isomer, reference compound in Lane 1) is not present in the polar *Petasites* extracts (Lanes 2 and 3) but is clearly present in the non-polar *Petasites* extracts (Lanes 4 and 5). Hence, *Petasites* extracts can clearly be distinguished into polar and non-polar *Petasites* extracts by the above-described TLC analysis.

Example 3—Determination of the Anti-Inflammatory Effects of a Non-Polar *Petasites* Extract on Human Nasal Epithelial Cells—Viral Stimulus Poly IC Methods: Primary human nasal epithelial cells from biopsies from turbinoplastic surgery were cultivated in human nasal epithelial cell basal medium (Promocell®) including antimycotics/antibiotics (1%) and gentamycin (0.5%). For the stimulation, cells were seeded on 6-well culture plates (250 000-170 000 cells/well) or 24-well culture plates (62 000-42 000 cells/well) in 1 mL basal medium and incubated for at least 12 h. Cells were then cultured for 24 h in 1 mL basal medium (untreated) or additionally stimulated with 10 μg/mL polyinosinic:polycytidylic acid (Poly IC) at 37° C. in the presence and absence of the non-polar *Petasites* extract "Ze 339" ("Tesalin") (3 μg/mL). The viral stimulant Poly IC is known to interact with toll-like receptor 3 (TLR3), which is expressed in the membrane of B-cells, macrophages and dendritic cells. Poly IC, as a viral simulant, therefore stimulates the immune system of the virus-infected host via the TLR3 pathway which is generally known to be involved in multiple inflammatory pathways (Lee J. et al., 2012, Cell, 151, 547-58). Experiments were iterated 8 times. Human nasal epithelial basal medium was used as a control. Measurement of cytokine and chemokine levels was performed as follows: Levels of CCL-5 were measured by ELISA (BD Bioscience) and (R&D Systems, Abingdon, U.K.). Levels of MIP-1β, IL-1 α, IL-6, GCSF, and TNF-α were measured using a multiplex assay (MILLIPLEX MAP Human Cytokine/Chemokine Magnetic Bead Panel). The assays were run as per manufacturers' instructions with standards and samples in duplicate, overnight incubation with shaking at 4° C. (18 h, 750 rpm) and using a hand-held magnetic block for wash steps. Data were acquired on a validated and calibrated Bio-Plex 200 system (Bio-Rad, USA) and analyzed with Bio-Plex Manager 6.0 software (Bio-Rad, USA).

Results: The administration of the non-polar *Petasites* extract "Ze 339" ("Tesalin") together with the viral stimulant Poly IC significantly reduced the expression levels of typical inflammatory cytokines GCSF, MIP-1β, IL-6, IL-1α, TNF-α and CCL5, when compared to the administration of Poly IC alone (see FIGS. 2 to 7). Therefore, *Petasites* extract demonstrated the lowering of the expressed amounts of virus-induced inflammation mediators ex vivo in live human nasal epithelial cells and is hence effective in the treatment of viral infections.

Example 4—Determination of the Anti-Inflammatory Effects of a Non-Polar *Petasites* Extract on Human Nasal Epithelial Cells—Viral Stimulus Poly IC LyoVec™ (InvivoGen, France)

Methods: Primary human nasal epithelial cells from biopsies from turbinoplastic surgery were cultivated as described in Example 3. The cells were stimulated for 24 h at 37° C. with polyinosinic:polycytidylic acid (Poly IC) LyoVec™ (InvivoGen, France) at 10 μg/mL in the presence and absence of 2 μg/mL of the non-polar *Petasites* extract "Ze 339" ("Tesalin"). The viral stimulant Poly IC LyoVec™ (InvivoGen, France) is a synthetic double-stranded RNA polymer which is sensed by the retinoic acid inducible gene I (RIG-1)/melanoma differentiation-associated protein 5 (MDA5) receptor in the virus-infected host, which functions as a pattern recognition receptor by recognizing double-stranded RNA, and is therefore a commonly accepted sensor for viruses (Gitlin L. et al., 2008, PNAS, 103, 8459-8464; Kato H. et al., 2005, Immunity, 23, 19-28; Kato H. et al., 2008, J. Exp. Med., 205, 1601-1610). Experiments were iterated 8 times. Human nasal epithelial cell basal medium was used as a control. Measurement of cytokine and chemokine levels was performed as follows: Levels of MIP-1α and IL-6 were measured using a multiplex assay (MILLIPLEX MAP Human Cytokine/Chemokine Magnetic Bead Panel). The assays were run as per manufacturers' instructions with standards and samples in duplicate, overnight incubation with shaking at 4° C. (18 h, 750 rpm) and using a hand-held magnetic block for wash steps. Data were acquired on a validated and calibrated Bio-Plex 200 system (Bio-Rad, USA) and analysed with Bio-Plex Manager 6.0 software (Bio-Rad, USA).

Figure 8:
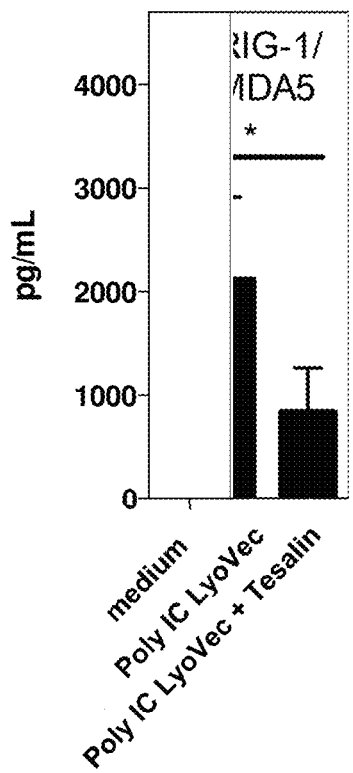
FIG. 8 shows the expression level of macrophage inflammatory protein 1α (MIP-1α) in nasal epithelial cells 24 h after administration of either polyinosinic:polycytidylic acid (Poly IC) LyoVec™ (InvivoGen, France) with or without co-administration of the non-polar *Petasites* extract "Ze 339" ("Tesalin"). The asterisks indicate a p-value of 0.05 at n=5-8.
Figure 9:
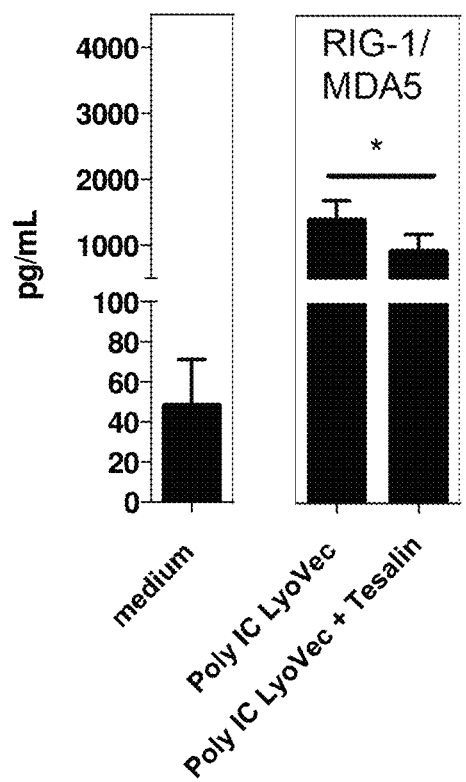
FIG. 9 shows the expression level of interleukin 6 (IL-6) in nasal epithelial cells 24 h after administration of either polyinosinic:polycytidylic acid (Poly IC) LyoVec™ (InvivoGen, France) with or without co-administration of the non-polar *Petasites* extract "Ze 339" ("Tesalin"). The asterisks indicate a p-value of 0.05 at n=5-8.

Results: The administration of the *Petasites* extract "Ze 339" ("Tesalin") together with the viral stimulant Poly IC LyoVec™ (InvivoGen, France) significantly reduced the expression levels of typical inflammatory cytokines MIP-1α and IL-6, when compared to the administration of Poly IC LyoVec™ (InvivoGen, France) alone (see FIGS. 8 and 9).

Therefore, *Petasites* extract demonstrated the lowering of the expressed amounts of virus-induced inflammation mediators ex vivo in live human nasal epithelial cells also for a different viral stimulant and is hence effective in the treatment of viral infections.

Example 5—Determination of the Anti-Inflammatory Effects of a Non-Polar *Petasites* Extract on Human Nasal Epithelial Cells—Bacterial Stimuli Pam(3)CSK(4), Flagellin and CpG-Oligonucleotide Methods: Primary human nasal epithelial cells out of biopsies from turbinoplastic surgery were cultivated as described in Example 3. Processing of cells and stimulation were performed under the same conditions as described in Example 3. Cells were specifically stimulated for 24 h at 37° C. with 200 ng/mL Pam(3)CSK(4), 5 ▫ g/mL Flagellin and CpG-oligonucleotide at 1-5 ▫ M in the presence and absence of 3 ▫ g/mL of the non-polar *Petasites* extract "Ze 339" ("Tesalin").

Results: The administration of the non-polar *Petasites* extract "Ze 339" ("Tesalin") together with the bacterial stimuli Pam(3)CSK(4), Flagellin and CpG-oligonucleotide showed no reduction in the expression level of the cytokines GCSF, MCP-1, IL-1▫, IL-6, IL-8, IP-10, and TNF▫, when compared to the administration of the bacterial stimuli alone. Therefore, *Petasites* extract is not capable of lowering the expressed amount of bacteria-induced inflammation mediators ex vivo in live nasal epithelial cells and is hence specifically effective in the treatment of viral infections.

In conclusion, *Petasites* extract is specifically reactive to virus-induced inflammations and typical bacterially activated inflammation pathways are not affected by the administration of *Petasites* extract.

The invention claimed is:

1. A method for the treatment of a viral infection in a mammal in need thereof, comprising the step of:
administering to the mammal in need thereof, an effective amount of a non-polar *Petasites* extract or composition comprising an effective amount of non-polar *Petasites* extract, wherein the effective amount of the non-polar *Petasites* extract or composition comprising the effective amount of the non-polar *Petasites* extract is effective in treating the viral infection.

2. The method of claim 1, wherein the non-polar *Petasites* extract is made by extraction with a non-polar solvent.

3. The method of claim 1, wherein the viral infection is a viral respiratory tract infection.

4. The method of claim 1, wherein the viral infection is a viral skin infection.

5. The method of claim 1, wherein the viral infection is a viral rhinitis.

6. The method of claim 1, wherein the viral infection is a viral sinusitis.

7. The method of claim 1, wherein the non-polar *Petasites* extract or non-polar *Petasites* extract composition has ≤2 ppm of pyrrolizidine-alkaloids.

8. The method of claim 1, wherein the non-polar *Petasites* extract is produced by extraction of the *Petasites* extract with liquid carbon dioxide.

9. The method of claim 8, wherein the non-polar *Petasites* extract is produced by extraction at subcritical temperature conditions.

10. The method of claim 1, wherein the non-polar *Petasites* extract is obtained from plants and/or parts of plants selected from the group of species consisting of *Petasites hybridus*, *Petasites albus*, *Petasites amplus*, *Petasites fragrans*, *Petasites formosanus*, *Petasites frigidus*, *Petasites georgicus*, *Petasites japonicus*, *Petasites laevigatus*, *Petasites kablikianus*, *Petasites niveus*, *Petasites paradoxus*, *Petasites pyrenaicus*, *Petasites tricholobus*, *Petasites radiates*, *Petasites sagittatus*, and *Petasites spurius*.

11. The method of claim 1, wherein the viral infection is selected from the group consisting of virus-caused chronic inflammatory airway diseases, virus-caused chronic sinusitis, virus-caused nasal polyps, rhinovirus infections, influenza and parainfluenza infections, respiratory syncytial virus (RSV) infections, adenovirus infections, Herpes virus family infections, herpes simplex infections, herpes zoster infections, rotavirus infections, enterovirus infections, coxsackie virus, and human papilloma virus (HPV) infections.

12. The method of claim 3, wherein the viral respiratory infection is selected from the group consisting of virus-caused upper aerodigestive tract and sinonasal diseases, otitis media with and without effusion, rhinitis, rhinosinusitis, gingivostomatitis, aphtosis, pharyngitis, tonsillitis, tonsillopharyngitis, laryngitis, tracheitis, bronchitis, bronchopneumonia, pneumonia, influenza, coryza, and common-cold.

13. The method of claim 4, wherein the viral skin infection is selected from the group consisting of herpes family type 1 and 2 infections, herpes zoster lesions, herpes infections in the context of atopic excema, molluscum contagiosum, human papilloma virus (HPV)-associated lesions, HPV-caused condylomata, and verrucae including high- and low risk serotypes.

14. The method of claim 1, wherein the non-polar *Petasites* extract or non-polar *Petasites* extract composition comprises a physiologically acceptable excipient.

15. The method of claim 1, wherein the non-polar *Petasites* extract or non-polar *Petasites* extract composition additionally comprises at least one ingredient from one of (I)-(VIII):
I. an antiphlogistic, analgesic, or antipyretic agent;
II. an extract of *Chamomilla recutita*, *Curcuma longa* rhizome, *Curcuma xanthorrhiza* rhizome, *Curcuma xanthorrhiza*, salicis cortex, *Salix purpurea*, *Salix daphenoides*, or *Tanacetum parthenium*;
III. trace elements, or salts of iron, iodine, copper; cobalt, magnesium, manganese, selenium, or zinc;
IV. secretolytic or secretomotoric agents, or extracts of licorice root, thyme, or peppermint oil;
V. bronchospasmolytic agents or extracts of ivy leaves, *Calendula* spp. or *Viola* spp.;
VI. vitamin A, C, D, E, or K or a B vitamin;
VII. antioxidants, lutein, zeaxanthin, bioflavonoids, or grape seed extract; and
VIII. taste mediators, an artificial or natural taste agent, or a sweetening agent, sugar or polyol sweetener.

16. The method of claim 1, wherein the non-polar *Petasites* extract or the non-polar *Petasites* extract composition is administered orally, topically, subcutaneously, intraperitoneally, intravenously, intra-nasally, or by inhalation.

17. The method of claim 1, wherein the non-polar *Petasites* extract or the non-polar *Petasites* extract composition is a dosage form selected from the group consisting of a spray, an aerosol, a foam, an inhalant, a powder, a tablet, a capsule, a soft gelatin capsule, a tea, a syrup, a granule, a chewable tablet, a salve, a cream, a gel, a suppository, a lozenge, a liposome composition or a solution suitable for injection, and a time-release or sustained-release dosage form of the above.

* * * * *